United States Patent [19]
Magnante et al.

[11] Patent Number: 5,579,063
[45] Date of Patent: Nov. 26, 1996

[54] METHODS AND DEVICES FOR THE MEASUREMENT OF THE DEGRADATION OF IMAGE QUALITY ON THE RETINA OF THE HUMAN EYE DUE TO CATARACT

[76] Inventors: Peter C. Magnante, 218 Wigwam Rd., West Brookfield, Mass. 01585; Leo T. Chylack, Jr., 15 Bradford Rd., Duxbury, Mass. 02331; David Miller, 9 Francis St., Brookline, Mass. 02146

[21] Appl. No.: 321,114

[22] Filed: Oct. 11, 1994

[51] Int. Cl.$^6$ ........................................................ A61B 3/10
[52] U.S. Cl. ............................ 351/211; 351/205; 351/221
[58] Field of Search ..................................... 351/205, 200, 351/211, 221, 209

[56] References Cited

U.S. PATENT DOCUMENTS 4,834,528  5/1989  Howland et al. ........................ 351/211

*Primary Examiner*—William L. Sikes
*Assistant Examiner*—Hung Xuan Dang

[57] ABSTRACT

Cataract and other diseases of the eye which degrade the clarity of the ocular media cause blurred vision and sensitivity to glare. Vision tests that require patients with unclear ocular media to read letter charts are not always reliable indicators of vision loss because these tests are sensitive to such subjective variables as patients' reading and language skills as well as neurological status. The invention provides a non-invasive means for the objective assessment of vision loss in patients with unclear ocular media thus overcoming the difficulties associated with subjective vision tests. The methods and devices of the invention provide the means for: 1) projecting the image of an external target source onto the patient's retina, 2) forming a second image of the retinal image of the target source onto the recording plane of an electronic camera, 3) transferring the electronic image to an image processing computer, and 4) measuring the extent of blurring of the retinal image of the target source with the computer. Vision loss is associated with the magnitude of the measured extent of the blurred retinal image.

6 Claims, 5 Drawing Sheets

METHODS AND DEVICES FOR THE MEASUREMENT OF THE DEGRADATION OF IMAGE QUALITY ON THE RETINA OF THE HUMAN EYE DUE TO CATARACT

BACKGROUND OF THE INVENTION

The invention relates to methods and devices for rapidly determining the sharpness of an image projected onto the retina of the eye. Since people who have cataracts or opacifications in their lenses or corneas complain of blurred vision even with corrective spectacles, the invention will be useful in assessing the extent of retinal image degradation experienced by these individuals and in serving as a guide for surgical intervention. As opposed to subjective vision tests, the objective tests performed with the invention do not require a verbal response from the subjects being measured.

1. Description of the Prior art

Every eye clinician qualitatively follows the progress of a patient's cataract by noting during routine ophthalmoscopic examinations how the details of fine line-like retinal blood vessels progressively blur. While these observations are useful in qualitatively assessing the extent of cataract development, they cannot easily be made quantitative since there is great variability among individuals in the size, shape and configuration of retinal blood vessels. Furthermore, simple visualization does not allow the clinician to quantify accurately the extent of blurring of the vessels.

The invention overcomes these difficulties by: 1) projecting the image of an external target source onto the patient's retina, 2) forming a second image of the retinal image of the target source onto the recording plane of a video camera, 3) transferring the electronic image to an image processing computer, and 4) measuring the extent of blurring of the retinal image of the target source with the computer. By these means, the invention provides an objective, accurate and rapid measurement of retinal image degradation due to cataract.

There are a number of optical instruments used in ophthalmic practice (including the ophthalmoscope and the slit lamp) that can be improved by the methods of the present invention in order to measure the extent of retinal image degradation due to cataract. These devices can be used to focus a test pattern on the retina, and permit the examining physician to observe the retinal image of the test pattern. Instruments of this type by Hardy, Rodenstock, Thorner, and Arnulf are described in the book by Y. Le Grand and S. G. El Hage entitled *Physiological Optics*, pp. 306–308, Springer-Verlag, 1980 (Berlin, Heidelberg & New York).

In Hardy's device, a target consisting of illuminated fine lines is located near the focal plane of a positive lens through which the subject views the target. The distance of the target from the lens is adjusted until the target is at maximum sharpness. This distance can be related to the spherical power correction needed by the subject. The fine line target can be rotated to check for astigmatism. In this device, the examiner looks directly into the subject's pupil without the aid of additional optical components.

Rodenstock's device is an improvement of Hardy's device. With it, the target remains fixed but its optical distance from the positive lens (through which the subject views the target) is varied through the use of a moveable reflecting prism. This device provides the examiner with a view of the image of the target on the subject's retina through the use of an afocal telescope. A focusing adjustment on the afocal telescope is linked to the prism's movement so that the image of the target on the subject's retina is simultaneously in best focus for both the subject and the examiner.

Thorner's device solves the problem of the bothersome corneal reflection of illumination light back to the examiner's eye which can interfere with the examiner's view of the retinal image of the target. The corneal reflection is eliminated by having the illumination light which forms the retinal image pass into the upper half semi-circle of the subject's pupil, and by having the returning light from the retinal image emerge from the lower half semi-circle of the subject's pupil. The two semi-circular sections of the pupil are properly apertured through the use of a pair of opposed semi-circular diaphragms in the instrument each of which is located conjugate to the appropriate half of the subject's pupil. One diaphragm is in the illumination section of the instrument while the other one is in the viewing section.

Arnulf's device uses a point source of light instead of a fine line source. Much less light enters the subject's eye with this small source and the problem of the corneal reflection is much reduced. Also, if astigmatism is present, there will be two focal positions of the instrument where sharp line-like retinal images of the point source will appear. Astigmatism can be determined by noting the focal positions of the instrument's focusing knob when sharp images of the two orthogonal line-like images are obtained. Point sources of light also have been used by Artal et al. to study such optical imaging defects in the normal eye as spherical and chromatic aberration ("Determination of the point-spread function of human eyes using a hybrid optical-digital method". Journal of the Optical Society of America A, vol.4, pp. 1109–1114 (1987); and "Optical Digital Procedure for the determination of white-light retinal images of a point test", Optical Engineering, vol. 28, pp. 687–690 (1989)).

The blurring of a line-like target on the retina of the human eye also has been measured by Campbell et al. and reported in "Optical and Retinal Factors Affecting Visual Resolution", Journal of Physiology, vol. 181, pp. 576–593 (1965), and "Optical Quality of the Human Eye", Journal of Physiology, vol. 186, pp. 558–578 (1966). In their measurements, a bright, fine line object was imaged on the retina. The light from the line image was reflected by the subject's retina back through his/her pupil and was re-imaged by an exterior lens onto a narrow, scanning slit positioned in front of a sensitive photomultiplier tube. As the slit scanned the retinal line image, the photomultiplier recorded its intensity profile, i.e. the linespread function (LSF). The scans were relatively slow making this approach unsuited for clinical applications where patient eye movement during a measurement scan will cause errors in the recorded LSF. In our invention, an electronic imaging device such as a vidicon or CCD camera coupled to a computer is used. This configuration results in the acquisition of a retinal image in 1/30 second which is the time required to capture and display a single video frame. The rapid image acquisition time, provided for in our invention, virtually eliminates problems due to eye movement.

SUMMARY OF THE INVENTION

Cataract surgeons assess visual impairment due to cataract through the use of subjective testing. With this type of testing, a patient responds to whether or not he or she can see on a chart certain letters or symbols of varying detail and contrast. A patient's performance on such a test depends on many factors including: 1) the quality of the optical image-forming components of the eye, 2) retinal pathologies that affect the sensitivity of the rods and cones, 3) neural problems that affect the transmission of visual stimuli from the retina to the brain, 4) psychological abnormalities, and 5) patient alertness and cooperation.

The subject of our invention is an instrument for the rapid measurement of the blur of projected line-like, bar-like or point-like targets on the retina of patients being evaluated for cataract surgery. The instrument, therefore, evaluates only the optical image-forming components of the eye. The optical measurements performed with the instrument are independent of the patient's neurological or psychological condition as well as his/her alertness and cooperation. The instrument provides an objective measurement which does not require the patient to respond to how well symbols on a vision testing chart are perceived.

Subjective vision testing now is used in assessing the overall contribution of both the optical components (i.e. cornea, aqueous, lens, and vitreous) and the non-optical components (i.e. photo-receptors, neural pathways, and the brain) in determining vision. In future, objective optical measurements will be used in assessing just the optical image forming components of the human eye. Results obtained with both types of test will be important to ophthalmologists for determining whether or not cataract surgery, which only corrects an optical defect, will improve a patient's overall visual function.

The objective optical test for measuring visual impairment due to cataract, which is the subject of this invention, is similar to a test used to evaluate inanimate lenses and lens systems such as photographic camera lenses. With it, the blurring of images of fine line-like objects formed on a screen (line spread function or LSF) by the less than perfect optical device is determined. The extent of blurring may be quantified, for example, by measuring the extent or linewidth of the LSF. Equivalently, the blurring may be quantified by determining the Modulation Transfer Function (MTF). The MTF is simply the Fourier transformation of the LSF. The Modulation Transfer Function and the method for its computation from LSF data are covered in the book by Warren J. Smith entitled *Modern Optical Engineering*, pp. 345–355, McGraw-Hill, Inc., 1990 (New York).

LSF testing of the human eye is somewhat different from testing inanimate lens systems (e.g. photographic camera lenses) because it necessarily requires the light forming the measured LSF to pass twice through the eye's optics (double-pass testing)—once in forming the primary LSF image on the retina, and twice in relaying the primary LSF image to form a secondary LSF image outside the eye onto the image plane of the instrument's video camera. In LSF testing of a photographic camera lens, on the other hand, the primary LSF image is formed directly on the recording and measuring device (single-pass testing).

The use and principle of the invention are based on line spread function (LSF) and Modulation Transfer Function (MTF) measurement methods which are used in optical technology to characterize the quality of images formed by optical systems. When measuring the human eye with these methods, the image of an illuminated narrow slit is projected onto the subject's retina where the slit image is focused as sharply as possible by the examiner. The secondary aerial image of the slit, which is formed outside the eye by the optics of the instrument, is relayed onto the image plane of a video camera. The camera transfers an electronic version of the image to an image-processing computer which determines the LSF (i.e. intensity profile of the aerial slit image on the image plane of the camera). The computer also can determine the MTF by calculating the amplitude Fourier transform of the LSF. The LSF and MTF are equivalent in describing the blurring of the retinal image, and either function is easily derived from the other through mathematical transforms,

BRIEF DESCRIPTION OF THE DRAWINGS

| FIG. | DESCRIPTION |
| --- | --- |
| 1 | Schematic of the Invention |
| 2 | Linespread Function (LSF) of Normal Young Eye |
| 3 | Correlation between Objective LSF Width and Extent of Nuclear Cataract determined from Appearance during Slit Lamp Examination |
| 4 | Correlation between Objective LSF Width and Subjective Minimum Angular Resolution (MAR) testing |
| 5 | Correlation between Objective MTF and Subjective Contrast Sensitivity (CS) testing |

DETAILED DESCRIPTION OF THE INVENTION

Our invention is innovative in that it provides the means for obtaining rapid, objective measurements of the Line Spread Function (and the related Modulation Transfer Function) of the human eye. Both the LSF and MTF are sensitive to the extent of intraocular light scattering; therefore, the invention is useful in assessing the degree of cataract formation and other ocular disease conditions associated with an abnormal degree of intraocular light scattering.

Description of Preferred Embodiment

Figure 1:
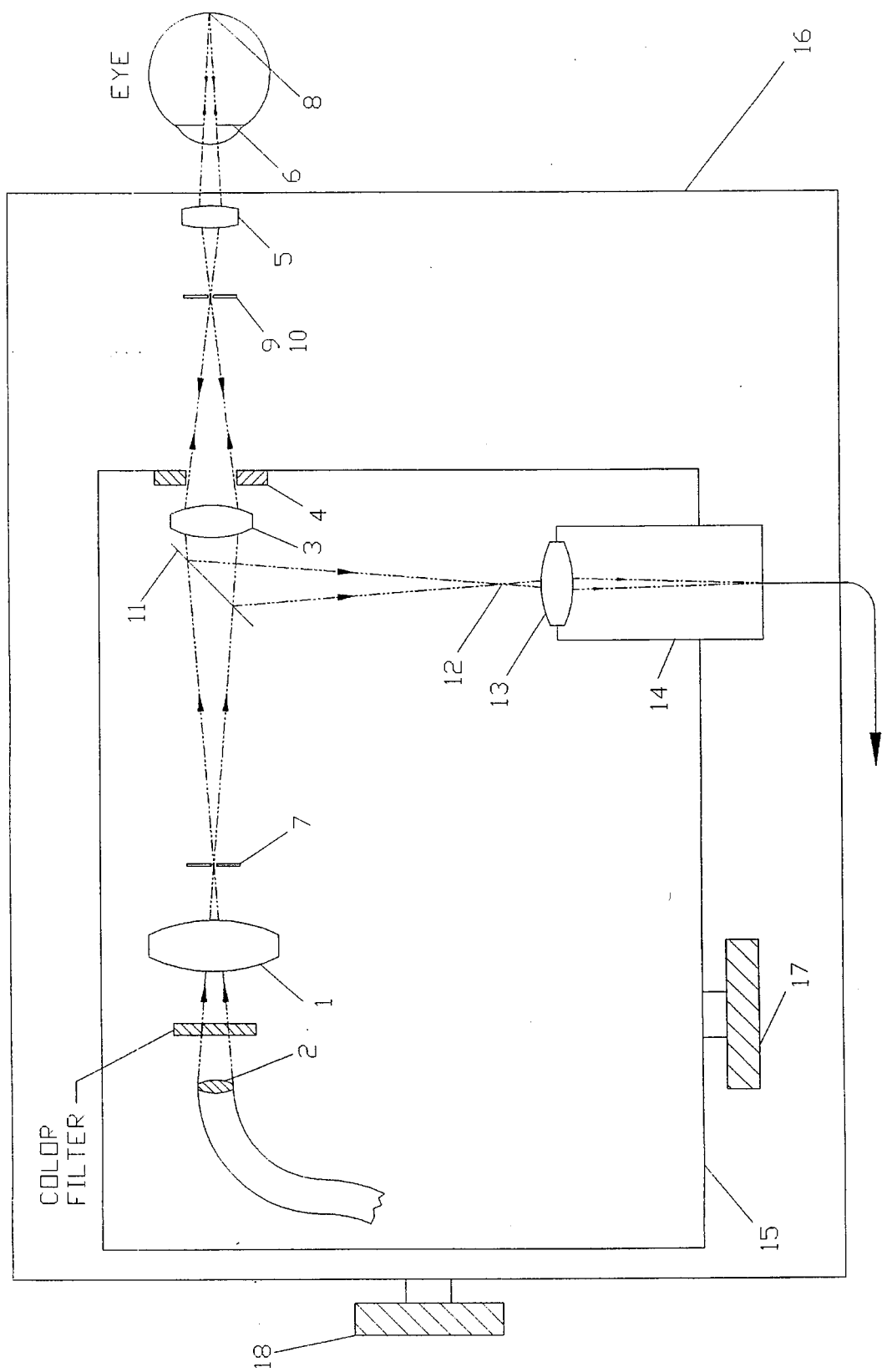

FIG. 1 is a schematic representation of a preferred embodiment of the invention. In this embodiment, the target projection optics and the LSF imaging optics are mounted on a common base. Also, the exit pupil of the target projection optics and the entrance pupil of the LSF image receiver optics are identical in this embodiment.

Condenser lens 1 forms an image of the light source 2 onto the projection lens 3 which has near it an adjustable aperture stop 4. A magnifying lens 5 relays an image of the aperture stop 4 onto the subject's pupil 6. Aperture stop 4 is adjustable (over a range from approximately 1 to 6 mm) and is used to set the diameter of the illuminating beam entering pupil 6 which is dilated with a mydriatic up to 8 mm in diameter. Measurements obtained with different aperture stop sizes are useful in assessing the effect of cataract location on vision loss.

Light source 2 can be a filament bulb or, for more uniform illumination of the projection lens 3, the distal end of an illuminated randomized fiber optic bundle, or a semi-transparent light diffusing plate. By these means, the light projected by the system into the subject's pupil 6 is both circular in shape and uniform in illumination.

Slit target 7 is placed close to condenser lens 1 so that it is uniformly illuminated. This is necessary to obtain uniform illumination of target images on the subject's retina 8. An image of the slit 9 is formed first by the projection lens 3, and is located in front of magnifying lens 5. The subject looks through magnifying lens 5 at slit image 9. The retinal image 8 of the bright slit image 9 is formed by both the magnifying lens 5 and the imaging optics of the subject's eye (i.e. cornea and lens). Small slits of several microns in width are used with subjects having relatively clear and low scattering ocular media. The retinal images of such narrow slits, even in subjects with very sharp vision, typically blur to more than 15 microns in width. For cataractous patients, the blurring is much larger than 15 microns. In extreme cases, the blurring is so large that the intensity of the LSF is too weak (when a very narrow slit is used) for a practical measurement. In such cases, the examiner can select a wider target slit in order to make the measurement.

Light from the retinal slit image 8 is reflected back to the subject's pupil 6, and emerges from the eye forming a secondary image of the slit 10. This reflected beam passes through the exact same aperture 4 that the incident beam passed through on its way to the subject's retina. Since aperture 4 defines the area of the subject's pupil 6 through which both the incident and the reflected light beams pass, it is guaranteed that the secondary slit image 10 is affected equally by both the incident light and the reflected light. This is so because both beams are constrained to pass through the same portions of the subject's cataract which are located behind the pupil 6. The ability to use the same aperture 4 for both the incident and the reflected beams is achieved by the use of beamsplitter 11 which makes the optics at the "front end" of the receiver optics (elements 3, 4, and 5) identical with the optics at the "exit end" of the illumination optics. With other optical systems having independent illumination and viewing systems, such as the slit lamp which does not use a common beam-splitter, this superposition of apertures is not possible.

The secondary image of the slit 10 is relayed by projection lens 3 and beamsplitter 11 to position 12 where a real image of the double-pass LSF is formed. Image 12 is relayed once again by close-up lens 13 to the image plane of the CCD camera 14 which captures the LSF image. A video monitor (not shown) connected to the CCD camera is used by the examiner to see the line image on the retina so that it may be optimally focused. The CCD camera's electronic signal is also sent through a cable to a video "frame-grabber" board which is installed inside a computer (not shown). The "frame-grabber" digitizes the image's intensity and location information which is contained in the CCD video signal, and stores the digitized image information in the computer.

The "frame-grabber" digitizes the image in the following way:

a) each point on the two-dimensional image is assigned an x-pixel integer (for horizontal direction) which typically ranges from 0–512, and a y-pixel integer (for vertical direction) which typically ranges from 0–460, and b) each location on the image (corresponding to x and y pixel values) has an intensity which is quantified by another integer scale that typically ranges from 0 (black) to 255 (very bright). The image is thus transformed into a kind of "topographical map" where the intensity level at a point in the image corresponds to a "height" on the map.

The computer processes and stores the raw digitized image data so that displays of the LSF may be viewed at any subsequent time. The computer also processes the digitized LSF data to obtain measures of the extent of retinal image blur due to cataract. Such measures include, for example, the linewidth of the LSF, and the MTF. The MTF is the amplitude Fourier transform of the LSF. The MTF characterization of an optical system is useful because it predicts exactly how the image contrast of periodic grid-like targets decreases as a function of the target's spatial frequency. The computer also is used to store all raw and processed data on disk, and to provide plots of these data.

All components of the device, except for magnifying lens 5, are mounted on an instrument base 15. Magnifying lens 5 is fixed on support surface 16. A chin and head rest (not shown) keeps the subject's head, and likewise eye, in fixed position. Instrument base 15 may be moved in and out (z-direction) with respect to the magnifying lens 5 by micrometer translation control 17. This movement allows the slit image to be focused optimally on the subject's retina 8.

Centering the instrument beam on the subject's pupil 6 is achieved by two separate adjustments. First, the patient's eye may be moved up and down (x-direction) with respect to the instrument beam by an adjustment on the chin and head rest (not shown). Second the instrument beam may be moved from side to side (y-direction) with respect to the subject's eye with micrometer translation control 18 which moves the support surface 16 with respect to the chin and head rest (not shown).

5.1.1 Dealing with Patient Refractive Spherical and Astigmatic Power Corrections If a patient has a refractive error, either with or without his/her corrective spectacles, the instrument must compensate for it otherwise the projected lines on the retina will be blurred not only by intraocular scatter but also by the refractive error. Spherical and astigmatic power errors are handled by the following techniques.

Spherical power is handled easily by carefully focusing the slit beam on the retina by moving the device toward or away from (z-axis) the magnifying lens 5 which itself is in fixed position with respect to the subject's eye. The sharpness of the slit image on the retina, as observed by the examiner, is the criterion for best focus. Focusing to an accuracy of ¼ diopter (for young individuals) and to ½ diopter (for older individuals) is achievable.

If a patient has any astigmatism, the sharpness of the slit image on the retina depends on the relative orientation between the slit-direction projected by the instrument and the axis of astigmatism of the patient's eye. The correction for astigmatism is handled easily by rotating the slit in its mounting. The operator rotates the slit slowly until the best focus of the slit image appears on the retina. When the slit is aligned in this way (along an axis of astigmatism), the image is sharper than for any other orientation. Astigmatic axes can be located to within ten degrees, and astigmatic power can be corrected to better than ½ diopter by this method.

5.1.2 Preferred Illumination Wavelengths

The retina in the vicinity of the macula is approximately 70–100 microns thick and is bounded posteriorly by the retinal pigment epithelium (RPE) and anteriorly by the inner limiting membrane (ILM). The thickness of the retina itself contributes a small amount to blurring the LSF. One such effect was demonstrated when we found that images formed in red light generally were more blurred than images formed in blue or green light. This red light "halation" is due to penetration of these longer wavelengths beyond the RPE layer into the choroid which has many diffuse scattering centers. The sharper line images for wavelengths in the range from 450–585 nm (blue to green) are due to the fact that these shorter wavelengths are strongly absorbed in the choroid. To avoid the red light "halation" problem, a preferred embodiment of the invention includes a "red-free" filter for the illumination light which only passes wavelengths in the range from 450–585 nm.

5.2 Description of Alternate Embodiments

Other optical instruments used in optometric and ophthalmic practice may be modified for objective LSF/MTF measurements in accord with the methods of the subject invention. Such instruments include the slit lamp microscope, optometers, ophthalmoscopes, retinoscopes, and ocular fundus cameras.

One such embodiment of the invention (although not preferred) consists of a conventional slit lamp microscope fitted with an accessory Hruby lens (−55 Diopter plano-convex lens). The Hruby lens is located approximately 75 mm in front of the slit lamp's nosepiece and just in front of the subject's eye. When the slit lamp is used without the Hruby lens, the primary slit image is formed by its projection lens approximately 100 mm in front of the instrument's nosepiece. The primary slit image, located in this way, normally is positioned within the subject's cornea, aqueous, or lens in order that these anterior structures may be examined critically with the instrument's microscope. When the slit lamp is used with the Hruby lens, the positive refractive power of the cornea is neutralized by the negative Hruby lens, and a primary image of the slit can be focused on the subject's retina. In addition, the Hruby lens forms a secondary virtual image of the retinal slit image (the double-pass LSF) approximately 100 mm in front of the microscope's nosepiece. The LSF is easily seen by the examiner viewing through the microscope. The best focus image of the LSF on the subject's retina is obtained by carefully adjusting the distance between the slit lamp and the stationary Hruby lens. The LSF image is relayed by the slit lamp's examining microscope onto the image plane of a CCD video camera which is mounted on the slit lamp. The camera is linked to an image processing computer for LSF data reduction and storage.

A problem with the slit lamp configuration arises because the illumination beam, as it converges to illuminate the Hruby lens, shows intensity variations due to the filament wires in the instrument's lamp. The Hruby lens collimates this converging beam for entry into the subject's pupil; however, the intensity variations tend to result in a non-uniform, irregular beam shape at the subject's pupil. This is a disadvantage which affects the accuracy of LSF measurements on cataractous eyes with inhomogeneously distributed opacities.

Another problem with the slit lamp and Hruby lens configuration arises because the instrument beam does not fill a subject's dilated pupil which generally has a diameter of from 6–8 mm. The average instrument beam diameter is only 2 mm. This small size is due to the focal lengths of the slit lamp's projection and Hruby lenses, and to the beam size at the projection lens. Although the 2 mm instrument beam will probe cataracts located within a millimeter of an axis through the center of the subject's pupil, it will not probe cortical cataracts located farther away from this axis.

There is another problem with the concave Hruby lens. Since concave lenses do not form real images, the Hruby lens is incapable of imaging the exit aperture of the slit lamp (located at the projection lens) onto the pupil of the subject's eye. This situation makes it impossible to form the desired sharply circular, uniformly illuminated beam at the pupil of the subject's eye.

5.2.1 Use of Alternate Targets and Associated Data Processing

The preferred embodiment of the invention includes the use of a narrow slit target. With a narrow slit, the blurred retinal image of the slit in a subject's eye is much wider than what the width of the retinal image of such a slit would be in an idealized eye that images perfectly without any blurring. As discussed above, the line spread function or LSF and the associated modulation transfer function or MTF are directly obtained from the light intensity distribution across the width of the retinal image of such a narrow slit.

Although the use of a narrow slit target is preferred, its use is not necessary. Instead of a narrow slit target, one can use a finite width bar-like target or, in general, any broad rectangular-shaped target. In fact, the use of several rectangular targets of either the same size or different sizes is an acceptable alternative to the preferred embodiment which uses a narrow slit target. If several rectangular targets are to be used, however, it is more convenient during subsequent data processing if the targets are oriented in the same direction (i.e. long edges are parallel to one another).

With the use of single or multiple rectangular targets, the optical, mechanical, electronic and computer components of the invention are exactly the same as what they are when a single narrow slit target is used, and have been described. The function of these components is to do the following: 1) optically project a target image on the retina, 2) optically image the retinal target image onto an imaging photoelectronic device, 3) transform the optical target image to an electronic signal representing the image, and 4) store the electronic signal in an image processing computer.

When one or several rectangular targets is used, the method of processing the image information is somewhat more complicated than is the case when a narrow slit target is used. The method of computer processing the data associated with the retinal image of a rectangular target (or targets) comprises the following steps: 1) determine the levels of light intensity at various points on the retinal image of the target, 2) determine the light intensity distribution at points along a line or lines that passes across pairs of parallel blurred edges of the retinal image of the rectangular target or targets. In step 2), it is usual to measure the blurring of those parallel edges which define the length, rather than the width, of the rectangle. The final step in the method of data processing to determine the extent of blurring of the retinal image of the target is either 3) to measure the linear extent of the light intensity distribution across the rectangular target or targets including their blurred edges, or 4) to find the modulation transfer function or MTF which is calculated by taking the amplitude Fourier transformation of the light intensity distribution across the rectangular target (or targets) including their blurred edges and then dividing that result by the amplitude Fourier transformation of a mathematically idealized light intensity distribution across the rectangular target (or targets) including their unblurred, perfectly sharp edges.

5.3 Comparisons of the Objective LSF Method to Subjective Vision Tests

In the following sections, correlations between objective LSF (and MTF) tests and several subjective vision tests are shown in order to demonstrate the utility of the new objective LSF/MTF method for assessing visual loss due to cataract formation. The human subjects who participated in the testing did not have neural impairments.

5.3.1 Similarity of Angular Dependence of Glare Disability and

Objectively Measured Linespread Functions

Figure 2:
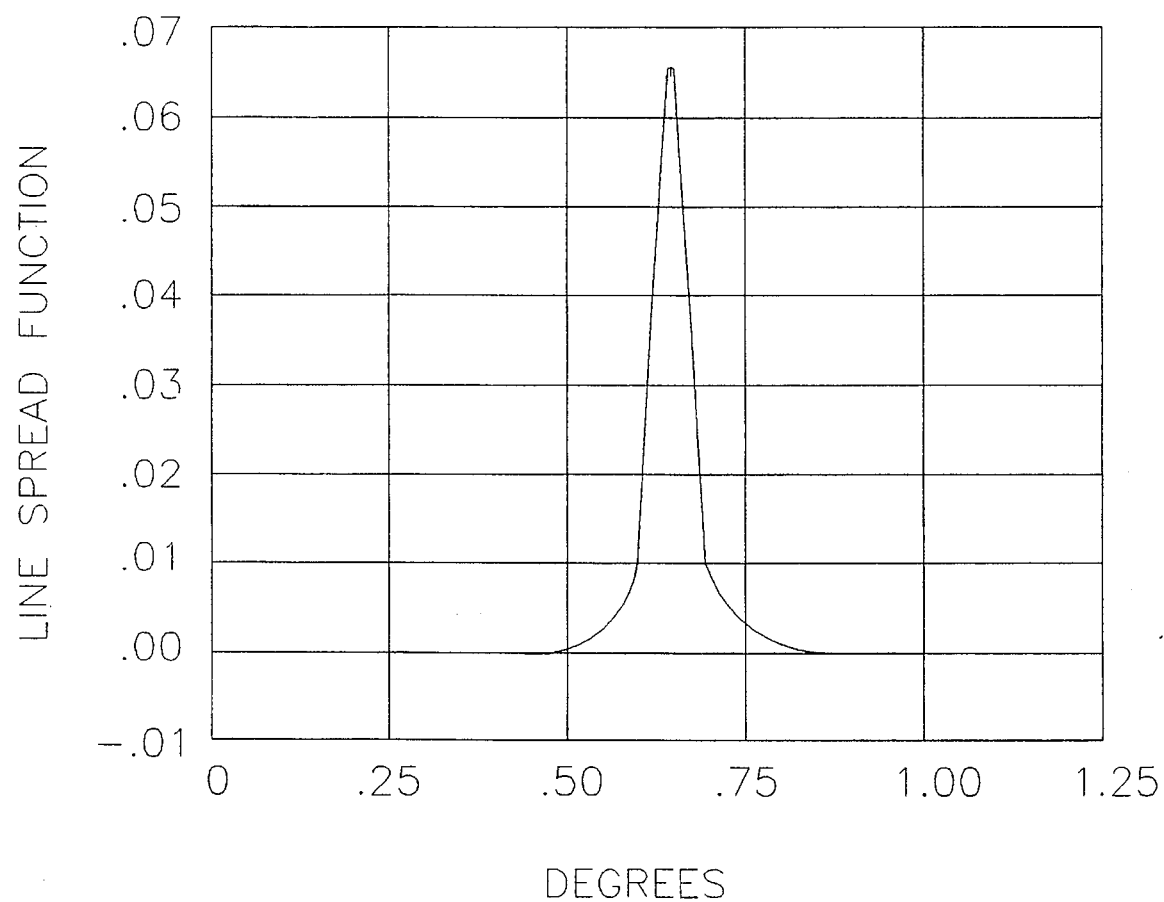

The dependence of glare disability on the angular location of the glare source with respect to the line of sight has been measured by R. P. Hemenger, *Applied Optics* vol. 23, pp. 1972–1974(1984). The angular dependence of disability glare determined from these psychophysical tests is very similar to the angular dependence of light scattered from the crystalline lens as measured by direct optical experiments on in-vitro lens sections by F. A. Bettelheim and M. Paunovic, *Biophysical Journal* vol. 26, pp. 85–99(1979). Data of J. Walraven in *Vision Research* vol. 13, pp. 1739–1753(1973) on young normal subjects show that light scattering by the optical media of the eye can blur the retinal image of a fine line by approximately 0.07 degree. The LSF, obtained using the methods of the subject invention, for the normal eye of a 24 year old subject is shown in FIG. 2. Note that the LSF has a width (full width at half height) of 0.06 degrees (3.6 minutes) which is in good accord with the subjective test result of Walraven.

Figure 3:
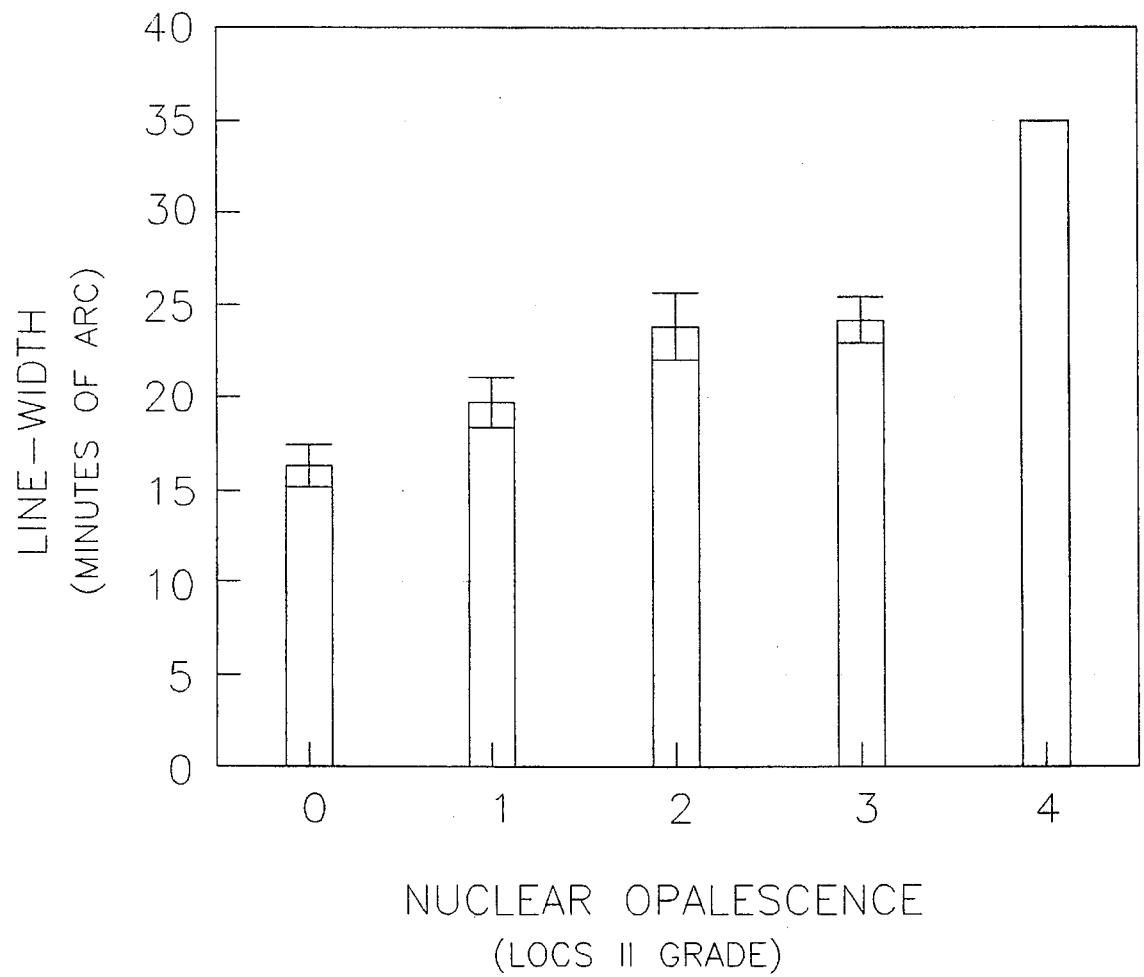

5.3.2 Correlation Between Objective Line Spread Function Width and Extent of Nuclear Cataract Determined from Appearance During Slit Lamp Examination Other data (Fig. 3) show that the widths of the LSF for 62 eyes with early to moderate nuclear cataract are significantly greater than for young normal eyes, and extend typically from 15–40 minutes of arc. These data also show a good correlation between LSF widths and the extent of the cataract. The measure of the extent of cataract is based on a clinical grading scale which depends on the degree of opalescence of the lens nucleus as observed during conventional slit lamp examination. Cataract severity is expressed on an integer scale ranging from 0 (no opalescence) to 4 (extreme opalescence). See "Lens Opacities Classification System II (LOCS II)" by Leo T. Chylack et al. in *Archives of Ophthalmology* vol. 107, pp. 991–997 (1989).

Figure 4:
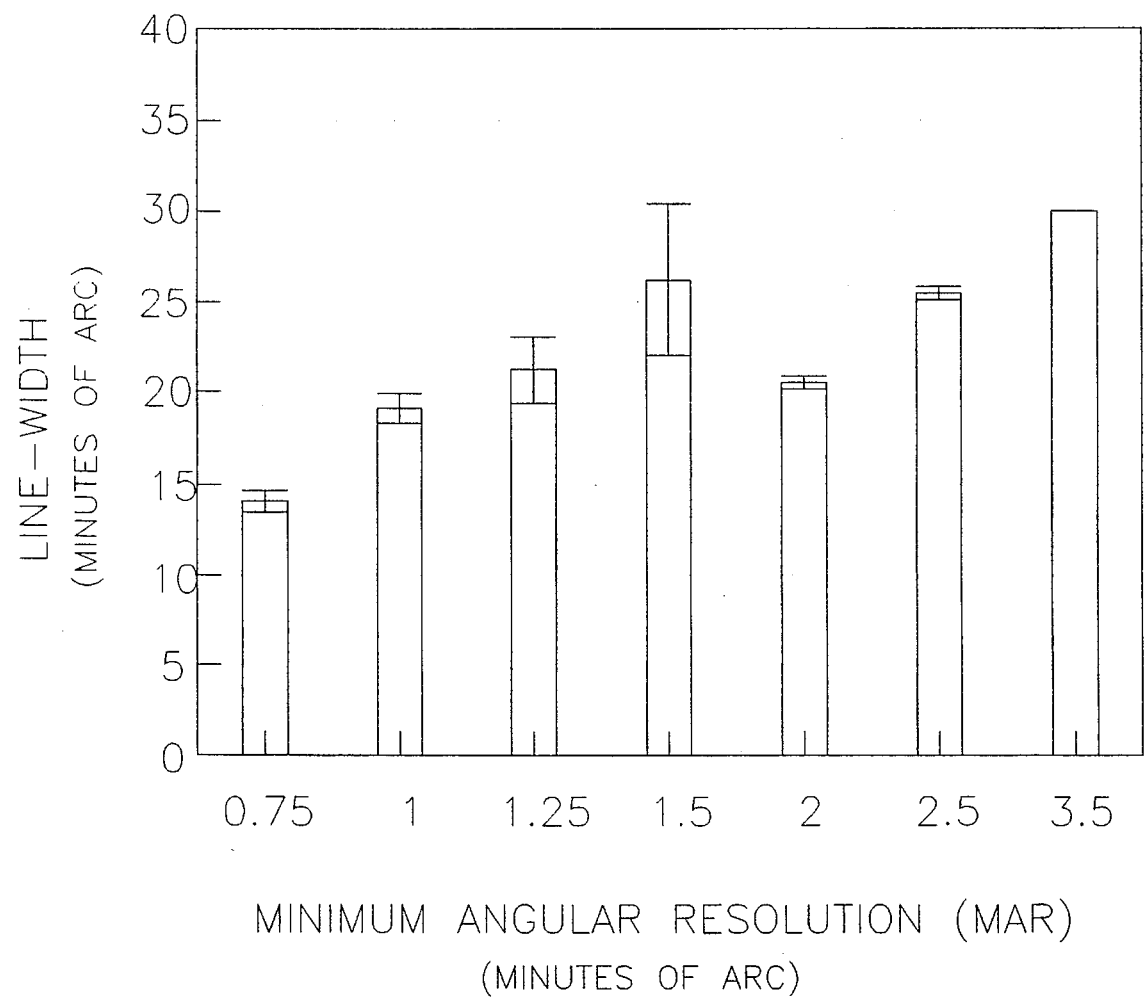

5.3.3 Correlation between Objective Line Spread Function Width and Subjective Minimum Angular Resolution Testing FIG. 4 shows data for 57 eyes with early to moderate cataract where the width of the objectively determined LSF (in arcmin) is plotted against the minimum angular resolution (MAR) score based on subjective Snellen acuity testing. The data include eyes with the following Snellen acuity (and equivalent MAR) scores: 1) 20/15 (MAR=0.75 arcmin), 2) 20/20 (MAR=1.00 arcmin), 3) 20/25 (MAR=1.25 arcmin), 4) 20/30 (MAR=1.50 arcmin), 5) 20/40(MAR=2.00 arcmin), 6) 20/50 (MAR=2.50 arcmin). and 7) 20/70(MAR=3.50 arcmin). The data show a good correlation between the objective and subjective vision tests.

Figure 5:
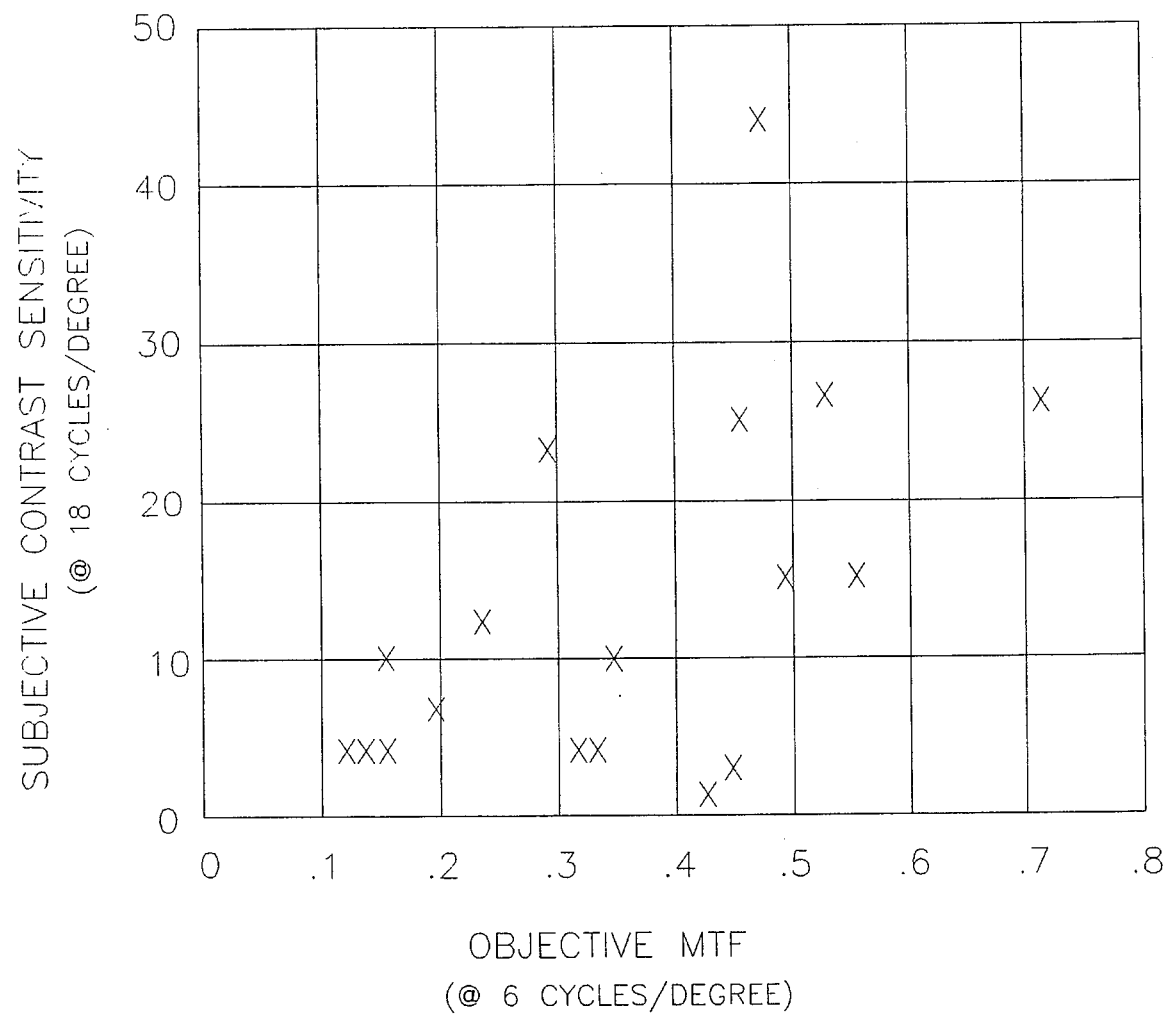

5.3.4 Correlation between Objective MTF and Subjective Contrast Sensitivity Testing FIG. 5 shows the correlation between objective MTF measurements, which quantify the blurring of fine lines projected on the retina, and subjective Contrast Sensitivity (CS) test results. These data are for twenty normal subjects with ages ranging from 24–64 years. For a conventional optical system (e.g. photographic camera lens), the MTF expresses the fraction of image contrast to target contrast for test targets of different spatial frequency (i.e. cycles per degree). In subjective vision testing, CS (for a specific spatial frequency) is the reciprocal of the contrast associated with a target on a test chart that is just at a subject's threshold of perception.

The correlations (shown in FIGS. 3, 4, and 5) of the objective LSF/MTF results with other test results that measure the extent of cataract development (e.g. cataract graded by slit lamp appearance, subjective Snellen acuity scores, and subjective Contrast Sensitivity scores) are evidence that objective LSF/MTF methods are effective in assessing visual function. Objective instrument and subjective vision tests correlate well for patients with normally functioning neural pathways extending from the retina to the brain. For patients with dysfunctional neural pathways, objective and subjective tests do not correlate as well. The two types of tests taken together are useful in distinguishing between the effect on vision of the optical elements of the eye, which extend from the cornea to the retina, and the neural elements associated with vision, which extend from the retina to the brain. In any case, the objective LSF/MTF method is important in assessing the contribution of the image forming elements of the cataractous eye to visual dysfunction problems such as loss of acuity, loss of contrast sensitivity, and glare disability.

We claim:

1. An ophthalmic device for measuring objectively the blurring of optical images projected on the retina of the human eye, including:

a) a target consisting of at least one rectangle, b) an optical projection system for imaging said target on the retina of the human eye, c) an optical image acquisition system for conveying the retinal image of said target back onto the image plane of a photo-electronic imaging device, d) a photo-electronic imaging device for transforming the retinal image of said target to an electronic signal which represents the image, e) a computer for processing the electronic image in order to obtain a measurement of the blurring of the retinal image of said target.

2. An ophthalmic device as claimed in claim 1 wherein said optical projection system and said optical image acquisition system consist of optical components commonly found in optometers, retinoscopes, ocular fundus cameras, and slit lamp microscopes equipped with external lenses.

3. An ophthalmic device as claimed in claim 1 wherein said photoelectronic imaging device is chosen from the group comprising vidicons, charge-coupled devices, and charge-injection devices.

4. A method for measuring objectively the blurring of optical images projected on the retina of the human eye, comprising the steps of:

a) optically projecting the image of at least one rectangular target on the retina of the human eye, b) optically conveying the retinal image of said target back onto the image plane of a photo-electronic imaging device, c) transforming the retinal image of said target to an electronic signal which represents the image by means of the photo-electronic imaging device, d) conveying said electronic image to a computer for data processing, and e) processing the electronic image with said computer in order to obtain a measurement of the blurring of the retinal image of said target.

5. A method as claimed in claim 4 where processing the electronic image in order to obtain a measurement of the blurring of the retinal image of said target comprises the steps of:

a) determining the levels of light intensity at various points on the retinal image of the target, b) determining the light intensity distribution at points along a line that pass across the blurred edges of the retinal image of the at least one rectangular target, and c) determining the extent of blurring of the retinal image of the target by measuring the linear extent of the light intensity distribution across the edges of the retinal image of the target.

6. A method as claimed in claim 4 where processing the electronic image in order to obtain a measurement of the blurring of the retinal image of said target comprises the steps of:

a) determining the levels of light intensity at various points on the retinal image of said target, b) determining the light intensity distribution at points along a line that pass across the blurred edges of the retinal image of the at least one rectangular target, and c) determining the extent of blurring of the retinal image of the target from the modulation transfer function which is found by calculating the amplitude Fourier transformation of the light intensity distribution across the at least one rectangular target including their blurred edges and then dividing that result by the amplitude Fourier transformation of a mathematically idealized light intensity distribution across the at least one rectangular target including their unblurred, perfectly sharp edges.

* * * * *